United States Patent [19]

Voorhees

[11] Patent Number: 5,749,099
[45] Date of Patent: May 12, 1998

[54] DRAINING DISPOSABLE FLUID-TIGHT EAR PROTECTOR

[76] Inventor: Donna Sue Voorhees, 3353 Rubio Crest Dr., Altadena, Calif. 91101

[21] Appl. No.: 847,003

[22] Filed: May 1, 1997

[51] Int. Cl.⁶ .................................................. A61F 11/14
[52] U.S. Cl. .............................. 2/209; 2/455; 128/866
[58] Field of Search ............................ 2/208, 209, DIG. 5, 2/455, 423, 174; 128/864, 866

[56] References Cited

U.S. PATENT DOCUMENTS

| 346,175 | 7/1886 | Shelby | 2/209 |
|---|---|---|---|
| 758,680 | 5/1904 | Otte | 2/209 |
| 2,198,546 | 4/1940 | Lover et al. | 132/45 |
| 2,378,398 | 6/1945 | Fiedler | 2/209 |
| 2,476,589 | 7/1949 | Driskill | 128/152 |
| 3,841,325 | 10/1974 | Pickard | 2/209 X |
| 4,134,153 | 1/1979 | Voorhees | 2/174 |
| 4,308,623 | 1/1982 | Voorhees | 2/209 X |
| 5,615,417 | 4/1997 | Jackson | 2/209 |
| 5,689,831 | 11/1997 | Harris | 2/209 |

FOREIGN PATENT DOCUMENTS

| 813532 | 9/1951 | Germany | 2/209 |
|---|---|---|---|
| 342384 | 2/1931 | United Kingdom | 2/209 |

*Primary Examiner*—Michael A. Neas
*Attorney, Agent, or Firm*—Philip H. Haymond; Emling & Associates

[57] ABSTRACT

A protective enclosure for the human ear which entirely encloses the ear except for a first opening sized to receive the outer ear and a second, lower, opening to act as a drain or weep hole, the weep hole having the ability to shed any liquid that is able to breach the enclosure. The first opening is surrounded by a band of pressure-sensitive adhesive to anchor the enclosure to the skin all around the base of the ear, forming a substantially fluid tight seal for the bag covering the ear. The opposite lateral edges of the enclosure are pleated inwardly to receive the operator's fingers in areas closely spaced to the adhesive while installing the enclosure over the ear.

8 Claims, 1 Drawing Sheet

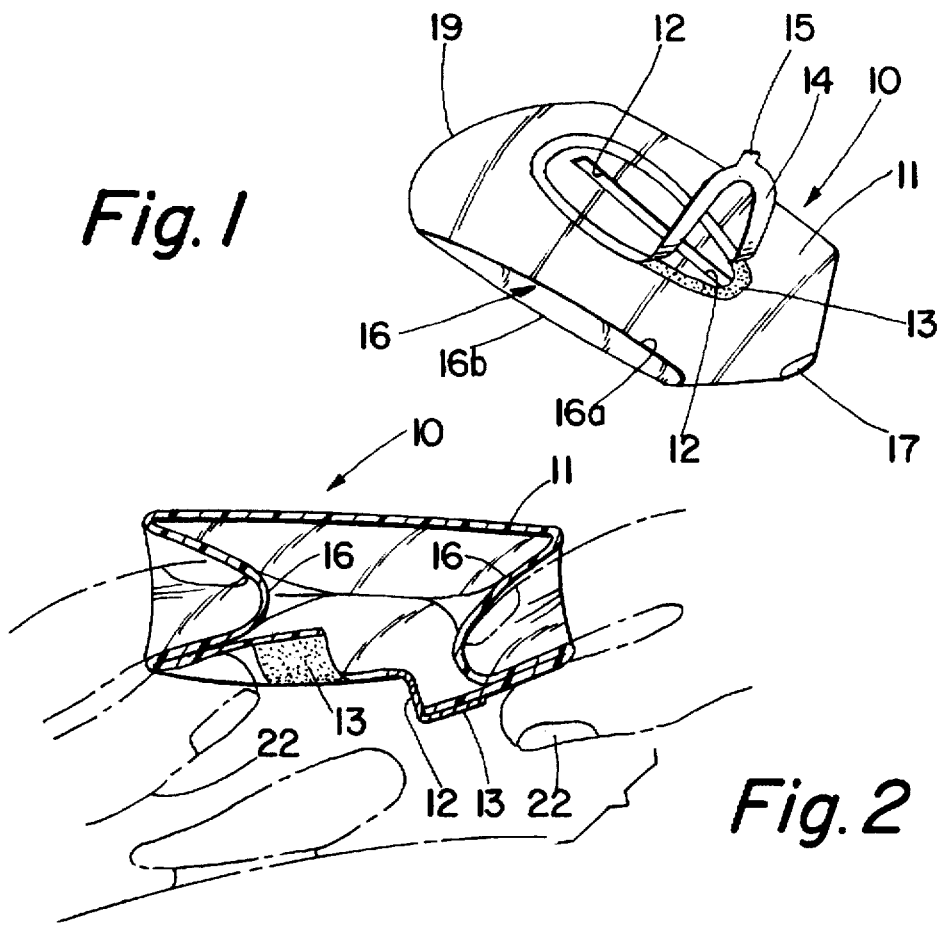
Fig. 1
Fig. 2
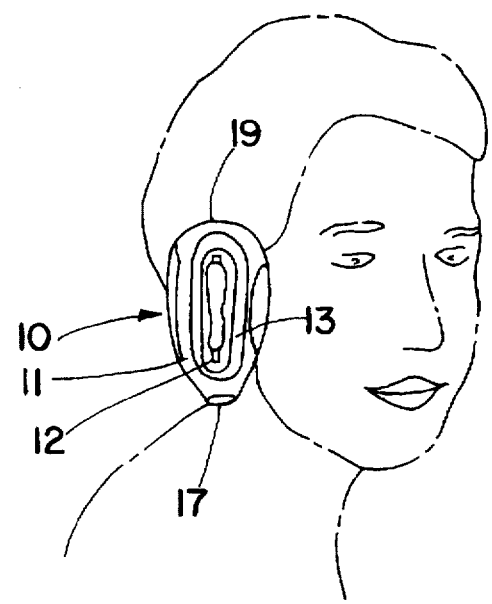
Fig. 3

DRAINING DISPOSABLE FLUID-TIGHT EAR PROTECTOR

FIELD OF INVENTION

This invention relates to the field of ear protection for persons having a medical condition that requires them to prevent water or other foreign matter from coming in contact with the pinna, or external ear, or from entering the auditory canal. This invention relates more particularly to an improved, inexpensive, single-use and substantially fluid-tight ear enclosure having an opening to receive the ear, that opening being lined by a layer of adhesive material to affix the ear enclosure to the skin surrounding the base of the ear, where the ear joins the skull.

BACKGROUND OF THE INVENTION

Many persons are afflicted with ear conditions that require them to exercise extreme caution against the entry of fluid or solid foreign matter on or into their ears. All necessary precautions must be taken to avoid exposure of the ear to a wide range of weather conditions, dust-laden air and moisture or fluids. Other common hazards include those encountered in bathing, taking showers, washing the scalp or having the hair dressed by a beautician unfamiliar with the risk incurred by such an afflicted person. An afflicted person may first need to protect their entire ear or ears before taking a shower, bathing and the like by placing a water-tight seal over the entire ear.

Various solutions have been devised to safeguard against the foregoing hazards and other hazards and are mentioned in the opening paragraphs of my own prior U.S. Pat. No. 4,134,153, issued Aug. 3, 1978. The ear protector construction disclosed in that patent avoids the numerous shortcomings and disadvantages of prior proposals, but was not as convenient to apply, nor as reliable and foolproof in excluding foreign matter as the ear protector of my second prior U.S. Pat. No. 4,308,623, issued Jan. 5, 1982.

My earlier patent, U.S. Pat. No. 4,134,153, employed a construction that used a single large plaque of plastic material assembled over the ear by gathering it from its opposite sides. Thereafter all edges were gathered together about the ear and secured by applying a rubber band, a twist wire or the like. However, if this operation was not performed with due care the gathered material could leak or become loose or untied at an inopportune time and expose the ear to serious hazards.

My second patent, U.S. Pat. No. 4,308,623, was an improvement over the prior art and avoided the disadvantages and shortcomings of the earlier devices, providing a highly reliable, inexpensive, single use ear protector. This protector comprised an envelope which was fully closed except for a single opening sized to receive the outer ear. Assembly of the envelope about the ear is aided and facilitated by providing its opposite edges with inwardly extending pleats to receive the user's forefingers and thumb to grasp the envelope closely adjacent the exposed adhesive material while guiding the ear through the opening. Thereafter the pleats enabled the forefingers to press a ringlet of adhesive firmly against the skin about the base of the ear to affix the ear protector over the ear, leaving the ear fully enclosed in a snug-fitting, substantially fluid-tight enclosure.

A problem with this and other devices of the prior art was that they sometimes allowed water to enter the ear protector if the user did not properly affix the ear protector to the surrounding skin. The adhesive strip would form an imperfect water-tight seal and allow some water to enter the ear protector. When this happened water could enter the ear protector and pool at the bottom of the ear protector and sometimes be splashed into the ear, in effect defeating any ear protection that the device was meant to provide.

A second problem with ear protectors of the prior art was that the adhesive strip displaced about the opening to receive the ear was generally asymmetrical in shape from top to bottom, in a "D" shape, this shape being complementing the general shape of an ear. The user was required to affix the straight length of adhesive in this "D" shape to the skin anterior to the base of the ear. Because of this asymmetry in the shape of the adhesive strip, the ear protector could be inadvertently applied backwards with the straight length of "D" shape of the adhesive strip affixed to the skin posterior to the base of the ear. The ear protector would then be in effect rotated 180 degrees from its proper orientation about the ear. The user would have to take care not to affix the ear protector "left handed" on the right ear and vice-versa.

Finally, ear protectors of the prior art are generally made from a heavier sheet plastic that is cumbersome and uncomfortable to wear.

Accordingly, it is a primary object of the present invention to provide an improved and inexpensive disposable protector for enclosing the ear to both preclude the entry of moisture and foreign matter and to drain the interior space of liquids or foreign matter should they somehow enter the ear protector.

Another object of the invention is the provision of an ear protector comprising a lighter film-like envelope of supple, impervious material having a first opening into its interior through which the ear is inserted and surrounded on its exterior by a band of pressure sensitive adhesive for sealing the opening to the surrounding skin at the base of the ear that can be applied without regard to the orientation of the adhesive strip.

These and other more specific objects will appear upon reading the following specification and claims and upon considering in connection therewith the attached drawings to which they relate.

SUMMARY OF THE INVENTION

The present invention is an ear protector comprised of an envelope which is fully closed except for a first opening on one side sized to receive the outer ear, a second opening at one end to act as a drain or weep hole when the second opening is worn on the ear oriented downwardly and affixing means for affixing the ear protector to the skin around the base of the ear.

The ear protector is retained on the ear with affixing means for affixing the ear protector over the ear. The affixing means can be comprised of many designs, such as an elastic band around the opening for receiving the ear, an adhesive strip or a series of adhesive spots around the opening for receiving the ear on the side of the envelope and the inventor does not intend to limit the scope of the claims by the preferred embodiment for means for affixing the ear protector to the skin around the base of the ear presented in this specification. The affixing means need only retain the ear protector over the ear while the exterior of the envelope is subjected to water or dust and more preferably to also form a substantially water-tight seal between the skin about the base of the ear and the envelope, to keep water or foreign matter from entering the ear protector. The preferred embodiment of the affixing means for affixing the ear protector over the ear is a continuous adhesive strip displaced about the opening for receiving the ear.

Assembly of the envelope over the ear is aided and facilitated by providing the ear protector's opposite edges with inwardly extending pleats to receive the user's forefingers and thumbs to grasp the envelope closely adjacent to exposed adhesive material while guiding the ear through the opening. Thereafter the pleats enable the forefingers to press a ringlet of adhesive firmly against the surrounding skin to affix the ear protector to the surrounding skin and over the ear, leaving the ear fully enclosed in a snug-fitting, substantially fluid-tight enclosure.

Should the user fail to properly apply the adhesive strip to the surrounding skin however, due to a lack of skill or an anatomical anomaly, any water that subsequently enters the interior of the ear protector by breaching the seal provided by the adhesive strip will harmlessly drain out the bottom of the ear protector through the lower opening or weep hole.

The preferred embodiment of the present invention is provided with an asymmetrical oval-shaped adhesive tab, narrower at the end proximal to the weep hole, to complement the shape of the surrounding skin about the ear. A first advantage of this shape is that it ensures a more secure fit of the ear protector to the surrounding skin. A second advantage of using an adhesive strip of this shape is that it alerts the user to correct orientation to fit the ear protector and hence ensures that the user will apply the ear protector with the weep hole oriented downwardly. It is crucial that the user wear the ear protector with the weep hole oriented downwardly because otherwise water could pool in the ear protector and also water would be let in through the weep hole should it be worn in an upward orientation.

In the preferred embodiment the adhesive strip is covered by a protective paper masking cover until such time as it is removed by the user to expose the adhesive for application. This masking cover is additionally equipped with both a tab at one end and the masking cover further has warning arrows or writing on it to ensure that the user is alerted to the correct orientation for fitting the ear protector.

The description of the embodiments of the apparatus and method claimed herein should not be construed as limiting and additional applications of this apparatus and method will be plain to one of ordinary skill in the art.

BRIEF DESCRIPTION OF THE DRAWING

Referring now to the drawing in which a preferred embodiment of the invention is illustrated:

FIG. 1 is a perspective view of an illustrative embodiment of the improved ear protector prior to use;

FIG. 2 is a cross sectional view through an ear protector in the process of being assembled to receive an ear; and FIG. 3 is a perspective view showing one of the protectors assembled to a person's ear.

DETAILED DESCRIPTION OF THE DRAWINGS

Referring to FIG. 1, there is shown an illustrative embodiment of the single use waterproof ear protector, designated generally 10. The protector is conveniently formed from seamless thermoplastic tubing such as polyvinyl chloride, polyethylene, or the like, optimally having a thickness of 0.3 to 1.5 mils. Plastic films of a wide variety of composition are suitable in practicing this invention because of their supple character and imperviousness to moisture and other foreign material. Another important characteristic is the ease with which the walls of such material can be heat-fused and sealed to one another.

A length of the plastic tubing 11 is provided with an elongated ear receiving opening 12. The area surrounding the rim of this opening is provided with a layer or strip of pressure sensitive adhesive 13 of a type well known in the adhesive art as non-reactive with or harmful to the skin. In the preferred embodiment the adhesive strip 13 is placed as closely to receiving opening 12 as manufacturing limitations will allow. A suitable adhesive meeting these requirements is obtainable from the Avery label company, the 3M corporation, or the Mercury Label Company, who make an adhesive identified as FC-290. This adhesive is firmly adherent to plastic 11 and is preferably protected until application to the skin by a masking cover 14 readily peelable from layer 13 at the time of use. Desirably, this mask includes a thumb-tab 15 extending beyond the edge of adhesive strip coating to facilitate its removal.

Preferably, the opposite lateral sides of each ear protector envelope are provided with an inwardly extending pleat 16. These pleats have a two-fold purpose, namely, permitting the protective enclosure 11 to expand to accommodate the outer ear without pressure by an envelope having an outer perimeter only slightly larger than the length and breadth of the ear and, secondly, greatly facilitating assembly of the envelope over the ear.

In the preferred embodiment the outer edges of inwardly extending pleat 16 are offset, with the opposite lateral side that has opening 12 forming the inwardly extending pleat at a point, shown at 16a, about 5 mm closer to the longitudinal midline of ear protector 10 than does the outer opposite lateral side, shown at 16b. In this manner the user is alerted to the presence of pleat 16, which might be otherwise overlooked because of the thin transparent plastic. In this manner pleat 16 is also made easier to spread by the fingers because the offset acts as a guide and a tab to open pleat 16.

After pleats 16 have been formed and envelope 11 has been flattened, a first opposite end 19 is sealed closed, such as by the well known heat-fusion technique, and it is preferably cut to an arcuate shape to accommodate the outer ear. The other or second opposite end is only partially closed with the opposite lateral sides cut and sealed to taper to the center of the second opposite end, forming weep hole 17. The tapering of plastic 11 at second opposite end helps to channel water into weep hole 17.

In the preferred embodiment the adhesive strip 13 is formed in an ovoid shape symmetrically displaced about opening 12 of ear protector 10, narrowing towards the opposite end having weep hole 17. This ovoid shape both better accommodates the anatomy of the ear and also serves to alert the user to which end has the weep hole and should therefore be oriented downwardly.

The affixing of the ear protector envelope 11 to an ear of the user is accomplished expeditiously and without need for tools, tie strings or fasteners of any kind. Pull tape 15 is lifted to separate mask 14 from the adhesive layer 13. Thereafter the user inserts either the thumb or forefinger of each hand into pleats 16 between the opposite ends of opening 12 with his one finger 22 pressing against the exterior of the envelope in the area outwardly of adhesive 13. The expanded envelope is then manipulated in the manner clearly illustrated in FIG. 2 to insert the outer ear through opening 12, with weep hole 17 oriented downwardly.

Once this has been accomplished, the pleats enable the user to press his finger further inwardly and run it along the area overlying the adhesive to ensure that the full length thereof is firmly pressed against and adherent to the skin surrounding the base of the ear. The entire outer ear is now substantially sealed from the elements by the envelope and foreign matter of neither a solid nor a liquid nature can enter the ear.

The user may proceed to wash and dress the hair, to take showers or any situation where water or foreign matter is present, except for the complete submersion of the ear in a liquid.

While the particular disposable fluid-tight ear protector herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. An ear protector, comprising:
   a) a supple envelope having a first distinct opening on a side for receiving an outer ear and tapering to form a second distinct opening on one end, and
   b) affixing means for affixing the ear protector to the skin around the base of the ear, whereby said second opening is worn oriented downwardly to act as a drain when said envelope is affixed over the ear.

2. The ear protector of claim 1 wherein the affixing means for affixing the ear protector over the ear is a continuous pressure sensitive adhesive strip.

3. The ear protector of claim 1 wherein the affixing means for affixing the ear protector over the ear is a plurality of spots of pressure sensitive adhesive.

4. The ear protector of claim 1 wherein the affixing means for affixing the ear protector over the ear is an elastic band.

5. The ear protector of claim 1 wherein the affixing means for affixing the ear protector over the ear is a continuous adhesive strip and the ear protector is tapered to form the second opening on one end to prevent water from pooling in the bottom of the ear protector.

6. The ear protector of claim 2 wherein the lateral sides of said envelope are pleated.

7. The ear protector of claim 6 wherein inward lateral edges forming pleats are offset.

8. The ear protector of claim 1 wherein said second opening has a diameter at its greatest dimension of less than one inch.

* * * * *